(12) United States Patent
Bushman

(10) Patent No.: US 6,328,877 B1
(45) Date of Patent: Dec. 11, 2001

(54) REFERENCE ELECTRODE IMPROVEMENT

(76) Inventor: James B. Bushman, 6395 Kennard Rd., Medina, OH (US) 44256

( * ) Notice: Subject to any disclaimer, the term of this patent is extended or adjusted under 35 U.S.C. 154(b) by 0 days.

(21) Appl. No.: 09/384,353

(22) Filed: Aug. 27, 1999

Related U.S. Application Data

(60) Provisional application No. 60/098,103, filed on Aug. 27, 1998.

(51) Int. Cl.$^7$ .............................. C23F 13/00; G01N 27/30
(52) U.S. Cl. ............... 205/775; 204/196.01; 204/196.36; 204/414; 204/435; 205/724
(58) Field of Search ..................................... 204/414, 435, 204/196.01, 906.02, 196.21, 196.36; 205/724, 725, 727, 734, 775

(56) References Cited

U.S. PATENT DOCUMENTS

| | | | |
|---|---|---|---|
| 2,760,922 | * | 8/1956 | Williams ................ 204/435 |
| 3,000,804 | * | 9/1961 | Cahoon et al. ............. 204/435 |
| 3,061,773 | * | 10/1962 | Ellison et al. ............. 204/196.02 |
| 3,142,631 | * | 7/1964 | Woodley ................ 204/196.02 |
| 3,159,783 | * | 12/1964 | Sparnaay et al. ............. 204/435 |
| 3,708,411 | * | 1/1973 | Vanslette ................ 204/435 |
| 3,833,495 | * | 9/1974 | Grubb ................ 204/435 |
| 4,959,138 | * | 9/1990 | Brinkmann et al. ............. 204/414 |
| 5,360,529 | * | 11/1994 | Edwards et al. ............. 204/435 |
| 5,397,452 | * | 3/1995 | Buck et al. ............. 204/435 |
| 5,490,916 | * | 2/1996 | Hall ................ 204/435 |
| 5,603,817 | * | 2/1997 | Settler ................ 204/435 |

\* cited by examiner

Primary Examiner—T. Tung
(74) Attorney, Agent, or Firm—Fay, Sharpe, Fagan, Minrich & McKee, LLP

(57) ABSTRACT

A system for measuring the effectiveness of cathodic protection or corrosion resistance comprises a coagulate-filled tube adapted for sensing electrical activity at a first end thereof. A second end of the coagulate-filled tube is in communication with a reference electrode. A voltmeter in communication with the electrode for supplying a reading of a voltage differential.

A capillary tube for use in conjunction with a reference electrode extends the reach of the reference electrode. A flexible conduit defines a continuous opening axially therethrough. The flexible conduit contains a conductive hydroscopic electrolyte coagulate such as gelatin or a crosslinked polymer. The conduit is adapted for communication at one end with an electrode that communicates with the coagulate. It is further adapted at a second end for sensing a level of electrical potential in proximity thereto.

9 Claims, 2 Drawing Sheets

REFERENCE ELECTRODE IMPROVEMENT

This application claims priority from U.S. Provisional Application Ser. No. 60/098,103, filed Aug. 27, 1998.

BACKGROUND OF THE INVENTION

The present invention is directed to the art of cathodic protection systems. It finds particular application in conjunction with reference electrodes used to monitor cathodic protection systems and corrosion and will be described with particular reference thereto. However, it is to be appreciated that the invention has broader application and may be advantageously employed in other environments.

Reference electrodes are used in cathodic protection work to evaluate the effectiveness of cathodic protection systems. They are also used with freely corroding structures to determine where the corrosion activity is the greatest. A reference electrode is commonly made from a pure metal immersed in a saturated solution of its own metal salt. In so doing, the energy level of that metal is stabilized. If the metal, in its saturated solution of its own salt, is placed in contact with a common electrolyte in which a metal component is either immersed or buried, one can measure the energy imbalance and know that all of the energy imbalance or change with time or from any known value is attributable to what is happening on the other structure and not with the reference electrode.

A copper/copper sulfate reference electrode is commonly used. A pure copper rod is immersed into a saturated solution of copper sulfate. The copper rod and saturated solution are placed inside of a plastic tube that has a porous plug tip in the end of it which permits the ions within the tube to come in contact with the ions in soil or water. The copper rod is contacted with a test lead of a voltmeter, and the other test lead of the voltmeter is connected to the structure to be tested. The porous plug tip is placed in contact with the earth and the energy imbalance is measured.

For example, if a measurement is made as just described on an underground steel pipe line, the structure will be in a freely corroding condition at an energy level of about half a volt. That would be −0.5 volts with respect to the copper/copper sulfate reference electrode. If the steel pipe line is brought under cathodic protection, that energy level will be raised to a value of about −0.85 volts. This is one of the criteria used for corrosion effectiveness. That is, an energy level shift to −0.85 volts will free the structure from all further corrosion. However, the readings are inconsistent. Different readings are produced based on where the reference electrode is placed. Hence, reference electrodes are often placed at permanent sites, most commonly down near the structure surface underground.

There are some problems associated with placing reference electrodes in the earth such as near the steel structure in question. For one, liquid electrolyte inside the cell will tend to permeate out into the surrounding environment with time. As a result, the cell becomes depleted, or, conversely contaminants are infiltrated into the cell so that there is no longer a pure copper rod in a saturated solution of only the pure metal salt. Impurities can react with a copper surface and contaminate the cell and cause its energy level to change. Various approaches are used to minimize that effect from happening, but none of them work very well.

Also, if the reference electrode is buried in the ground, it will not be known when the actual energy level has started to change on the reference electrode. Moreover, the presence of the electrode so close to the structure being monitored can interfere with cathodic protection to the device. If the solution leaks out, it can increase the corrosion of the steel.

Little has been done to improve upon the negative aspects of electrodes used for monitoring cathodic protection or corrosion. One attempt, however, has been to run a capillary tube or luggin probe (i.e., a small tube or capillary filled with electrolyte that terminates near to the metal surface under study and used for the purpose of providing an ionically conducting path without diffusion between an electrode under study and a reference electrode) down from the surface of the earth to the location right next to a permanently installed reference electrode. That capillary tube is filled with a liquid electrolyte. A reading can be made through that capillary tube moisture path. In such a system, a reference cell is placed at the top of the tube and contacted with the moisture path provided by the capillary tube. A reading can be made down through the plastic tube to the reference cell down in contact with the earth to measure the energy imbalance between the tube and cell. The reason for this apparatus is that if there were a cell up at the top of the earth and another one down in the earth about four or five feet away, there could be a natural voltage gradient in the earth that would distort the reading. Without the capillary tube, it is virtually impossible to determine an error in the reading. By using the tube, the reading is actually made between the tip of the tube down in the earth and the cell that was buried there.

There are a number of problems with this structure that employs a capillary tube or luggin probe. Liquid electrolyte poured down the tube evaporates or leaks out over time. It is necessary to keep replenishing it. This is a cumbersome process that many would prefer to avoid. Also, the permanent cell placed down in the earth is an expensive item. It may cost around $50 to $150 to manufacture.

In order to overcome the cumbersome and uneconomical aspects associated with using the capillary tube, it is desirable to develop an improved capillary tube that will reduce the possibility of electrolyte leakage therefrom. Further, it is desirable to develop a capillary tube that can remain in place for an extended period of time without replacement.

The present invention contemplates a new and improved reference electrode capillary tube which overcomes the above-referenced problems and others.

SUMMARY OF THE INVENTION

In accordance with the present invention, there is provided a reference electrode capillary tube that contains a thick, gelatinous electrolyte that allows electrical contact between an above ground reference electrode and a sensing point beneath the surface of the earth.

In accordance with a more limited aspect of the invention a system for measuring the effectiveness of cathodic protection or corrosion resistance comprises a coagulate-filled tube adapted for sensing electrical activity at a first end thereof. A second end of the coagulate-filled tube is in communication with a reference electrode. A voltmeter in communication with the electrode for supplying a reading of a voltage differential.

In accordance with a still more limited aspect of the invention, a capillary tube for use in conjunction with a reference electrode extends the reach of the reference electrode. A flexible conduit defines a continuous opening axially therethrough. The flexible conduit contains a conductive hydroscopic thixotropic electrolyte coagulate such as a gelatin or a crosslinked polymer therein. The conduit is adapted for communication at one end with an electrode that communicates with the coagulate. It is further adapted at a second end for sensing a level of electrical potential in proximity thereto.

One advantage of the invention is that the coagulate or gel inside the capillary tube does not leak or permeate out of the capillary tube. This does away with the need for repeated refilling of the tube with a non-viscous liquid electrolyte. It also prevents underground contamination from occurring, or even increased corrosion to the metal structure. The gel-filled capillary tube does not interfere with cathodic protection to the metal device.

Another advantage of the present invention is that the capillary can remain in place. Once can come along with a portable reference electrode to periodically monitor any change or imbalance in the voltage.

Still further advantages of the present invention will become apparent to those of ordinary skill in the art upon a reading and understanding of the following detailed description of the preferred embodiment.

BRIEF DESCRIPTION OF THE DRAWINGS

The invention may take part in various parts and arrangement of parts. The drawings are only for purposes of illustrating a preferred embodiment and are not to be construed as limiting the invention.

DETAILED DESCRIPTION OF THE PREFERRED EMBODIMENT

Figure 1:
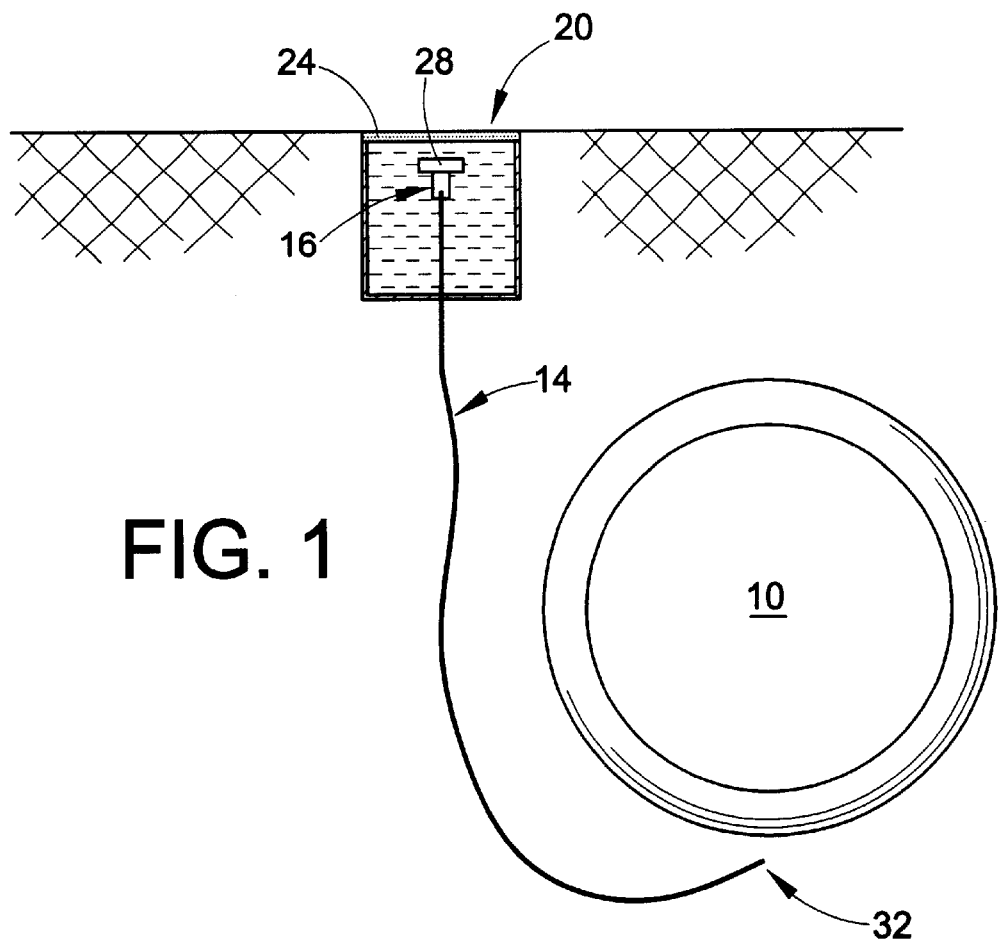
FIG. 1 is a schematic representation of a system for monitoring a corrosion protected underground storage tank that is in place prior and subsequent to insertion of a portable reference electrode.

With reference to FIG. 1, a system for monitoring a corrosion protected underground storage tank 10 includes a coagulate or gel-filled flexible plastic tube 14, a coagulate or gel filled testing chamber 16, and a soil surface mounted test box 20. The lid 24 of the test box 20 is shown here in a closed position. The gel filled tube 14 is inserted and sealed into the testing chamber 16. The testing chamber is comprised of a small container with a sealing, removable cap 28. The test box serves to protect the testing chamber from the surrounding elements, and the access door or lid 24, when opened, provides a route for a reference electrode to be manually inserted for testing purposes. The distal end 32 of the capillary tube 14 is shown in FIG. 1 to be near but removed from the underground storage tank. Optionally, a porous end cap, such as a ceramic or wood plug may be placed at the tip or end 32 of the tube 14 to minimize ion exchange into our out of the tube.

Figure 2:
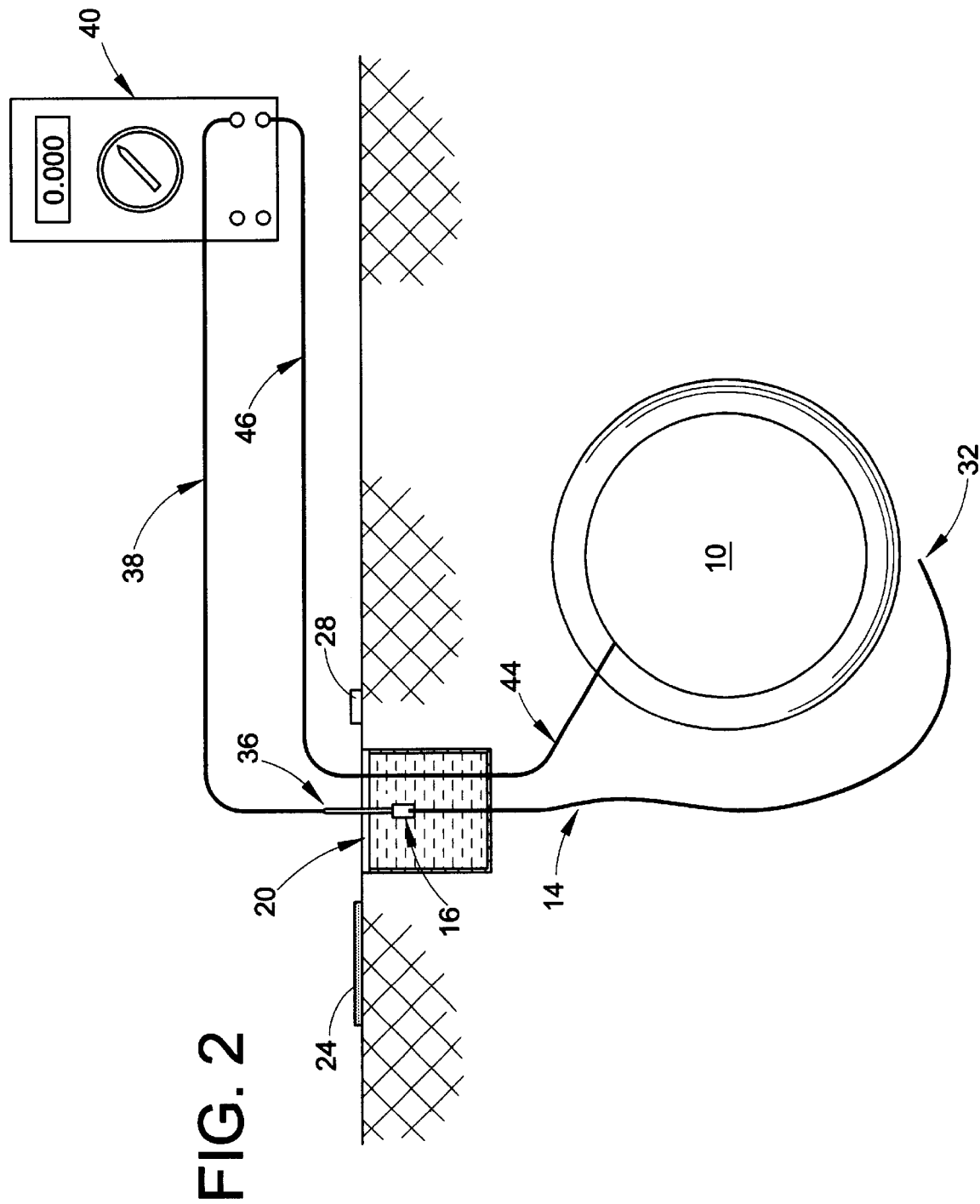
FIG. 2 is a schematic representation of the system of FIG. 1 with a reference electrode in place.

As will be noted in FIG. 2, when it is desirable to test the underground storage tank, the lid 24 to the soil surface mounted test box 20 is opened and removed, as shown. Next, the cap 28 to the gel filled chamber is removed. A portable reference electrode 36 having a porous tip is inserted into the gel filled chamber 16 in order to make a reading. The sensing point for the reference electrode is at the end 32 of the gel filled tube positioned under the storage tank. It should be noted that this drawing is only provided by way of example. It is forseeable and within the scope of the invention that the sensing end may be in contact with the ground, a metal or other surface, or another electrode either under the ground or under water.

A test lead wire 38 is connected to the portable reference electrode 36 from a DC terminal of a voltmeter 40. The voltmeter can make a permanent or temporary connection to the structure being tested. If it is permanent, the lead 44 is terminated in the test box 20 and a temporary test lead 46 is connected to this from the voltmeter (negative or common) terminal as shown in this example. After the reading is taken, the reference electrode is removed and the voltmeter is disconnected. The gel filled capillary tube remains in place. Of course, it is fully forseeable that the tube can be removed and re-positioned at the time of the next reading. However, by leaving it buried under the ground, there is a significant savings in time and in accuracy of the readings. The electrolyte gel or coagulate in the capillary does not require refilling and maintains its effectiveness without dire consequences to the surrounding environment. Ideally, a portable reference electrode is used and the top end of the capillary tube remains in the capped and sealed gel filled chamber until the next reading.

Figure 3:
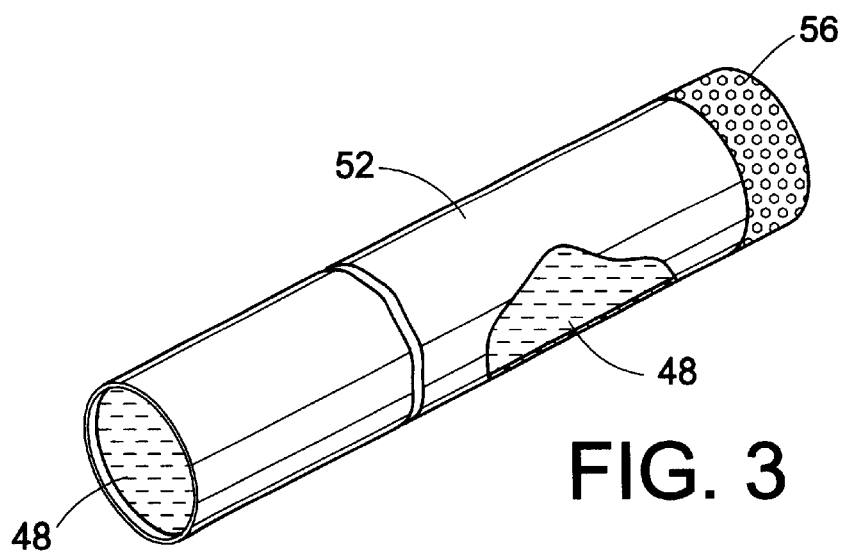
FIG. 3 shows a segment of the capillary tube of the filled present invention, with a portion of the tube broken away to show the gel inside.

With attention now on FIG. 3, a gel or coagulate electrolyte 48 is placed inside of a small diameter plastic tube 52. The tube could be 1/32" in diameter or less or as great as 2" in diameter or more. The most preferable or useful size is in the range of about 1/8" to 1/2" diameter tubing. The small 1/32" tube is fine for smaller distances. The tubing itself is a flexible polymer or rubber and made to be the length that is desired. The electrolyte gel in the tube extends the reach of the anode far beyond its placement or location. The electrolyte gel in the capillary tube enables accurate readings at great distances. It enables the use of portable cells. The tip of the portable cell is touched to the top of the tube that has the gel in it. It reads down through the gel to the bottom of the tube which is located at or near the structure or point of interest either underground or underwater. The gel tube is economical, costing only a fraction (less than 10–20%) of the permanent cell.

The gel containing tube provides an accurate reading since it does not become contaminated. It is simply a salt bridge that enables a measurement to be taken therethrough. The use of anti-freeze in the gel or in or around the tube prevents freezing and enables use of the tube throughout the year. It is also foreseeable to insulate the gel tube against the elements.

The gel electrolyte is placed inside of a plastic tube. At one end there is a porous plug 56, such as a ceramic plug or even a wooden plug. The porous plug allows the surrounding moisture and the salt to make contact with the gelled moisture in the tube. Alternatively, one could run a string or thread up through the tube along with the gel to ensure that if any air gaps exist, the ions would be able to jump across the air gap by capillary action through the moistened thread. As a third alternative, a permanent reference electrode could be located at the top of the tube to speed up the reading even further. While this alternative would cost more, the reading would be taken quicker and the accuracy of the electrode could be easily checked. Also, the electrode could be easily replaced if its accuracy had diminished.

The preferred coagulate used in the capillary tube comprises gelatin but it is forseeable that a polymer (i.e., a crosslinked polymer) could be used. Gelatin or gel is typically obtained from a controlled hydrolysis from the fibrous insoluble protein collagen. This is typically found in nature as a major constituent of skin, bones and connective tissue. Since it is a protein, gelatin has a unique sequence of amino acids glycine, proline and hydroxyproline. Commercial gelatins comprise a heterogenous protein mixture of polypeptide chains. Gelatin molecules are large and have a molecular weight ranging from a few thousand to several hundred thousand Daltons. The molecular weight distribution of the gelatin has an influence on its properties including its viscosity.

The thixotropic coagulate component that is useful in the present invention covers not only gelatin gels, but extends to crosslinked polymers having the same or similar characteristics. The characteristics of the gelatin, or crosslinked polymeric thickening agent should provide for a thickened conductive electrolyte within a tube to the point where it does not deleteriously leak out during the life of the sensor tube (5 to 30 years) and has the following characteristics:

Electrical resistivity less than 1000 ohm-cm;

Freezing point less than −15° C.;

Liquefying point greater than 45° C.;

Viscosity greater than 1000 CP;

Hydroscopic.

The useful or ideal viscosity will vary with the diameter of the tube. In general, the thinner the tube, the thinner the useful viscosity of the gel can be.

The gel or other coagulate must be hydroscopic, i.e., it must be such that it attracts and retains moisture. One example of a useful electrolyte gel for the present invention is one that contains calcium chloride.

The invention has been described with reference to the preferred embodiment. Obviously, modifications and alterations will occur to others upon a reading and understanding of the preceding specification. It is intended that the invention be construed as including all such alterations and modifications insofar as they come within the scope of the appended claims or the equivalents thereof.

I claim:

1. A system for measuring the effectiveness of cathodic protection or corrosion resistance of an underground metal structure, comprising:

a flexible tube buried in the ground long term, a first end thereof at or near the metal structure to be tested;

a second end of the flexible tube in communication with a reference electrode located at the surface of the ground;

a voltmeter in communication with the electrode and the metal structure for supplying a reading of a voltage differential;

a hydroscopic conductive electrolyte coagulate having a freezing point less than −15° C. and liquefying point greater than 45° C. which fills the flexible tube.

2. The system of claim 1 wherein the coagulate in the tube comprises a substance having electrical resistivity less than 1000 ohm-cm.

3. The system of claim 1 wherein the coagulate in the tube comprises a substance having a viscosity greater than 1000 CP.

4. The system of claim 1 wherein the coagulate in the tube is a gel.

5. The system of claim 1 wherein the coagulate in the tube is a polymer substance.

6. The system of claim 1 wherein a string or thread runs through the length of the coagulate-filled tube to provide a continuous ion conduction path across inadvertent air gaps for ion conduction along the length of the tube.

7. The system of claim 1 wherein the first end of the filled flexible tube is closed by a porous plug.

8. The system of claim 1 wherein the second end of the flexible tube is sealed within a coagulate or gel-filled chamber having a removable cap covering an opening through which a reference electrode is adapted to be inserted, the reference electrode being in communication with the electrolyte coagulate in the tube.

9. A method for testing effectiveness of a cathodic protection system, comprising the steps of:

filling a flexible conduit with a viscous coagulate electrolyte having a freezing point less than −15° C. and liquefying point greater than 45° C.;

placing a first end of the filled flexible conduit in a location underground or underwater where it is desired to sense conductivity;

maintaining the conduit underground for a long term;

transferring ions from the first end of the tube through the coagulate to a second end of the tube;

communicating a second end of the coagulate-filled tube with an electrode at the surface of the ground; and measuring a voltage differential at a surface position.

* * * * *